(12) United States Patent
Stensrud et al.

(10) Patent No.: US 9,464,026 B2
(45) Date of Patent: *Oct. 11, 2016

(54) RECOVERING AND USING CARBOXYLIC ACIDS FROM A FERMENTATION BROTH

(71) Applicant: Archer Daniels Midland Company, Decatur, IL (US)

(72) Inventors: Kenneth Stensrud, Decatur, IL (US); Padmesh Venkitasubramanian, Forsyth, IL (US)

(73) Assignee: ARCHER-DANIELS MIDLAND COMPANY, Decatur, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/650,453

(22) PCT Filed: Dec. 9, 2013

(86) PCT No.: PCT/US2013/073783
§ 371 (c)(1),
(2) Date: Jun. 8, 2015

(87) PCT Pub. No.: WO2014/099429
PCT Pub. Date: Jun. 26, 2014

(65) Prior Publication Data
US 2015/0321990 A1   Nov. 12, 2015

Related U.S. Application Data

(60) Provisional application No. 61/739,769, filed on Dec. 20, 2012.

(51) Int. Cl.
| | |
|---|---|
| C07C 69/00 | (2006.01) |
| C07C 67/08 | (2006.01) |
| C12P 7/44 | (2006.01) |
| C07C 29/149 | (2006.01) |
| C12P 7/40 | (2006.01) |
| C12P 7/42 | (2006.01) |
| C12P 7/46 | (2006.01) |
| C12P 7/48 | (2006.01) |

(52) U.S. Cl.
CPC ............ *C07C 67/08* (2013.01); *C07C 29/149* (2013.01); *C12P 7/40* (2013.01); *C12P 7/42* (2013.01); *C12P 7/44* (2013.01); *C12P 7/46* (2013.01); *C12P 7/48* (2013.01); *Y02E 50/343* (2013.01); *Y02P 20/544* (2015.11)

(58) Field of Classification Search
CPC ... C07C 67/08; C07C 29/149; C07C 31/207; C07C 69/40; C07C 69/675; C07C 69/704; C12P 7/44; C12P 7/46; C12P 7/48; C12P 7/40; C12P 7/42; Y02E 50/343; Y02P 20/544

See application file for complete search history.

(56) References Cited

U.S. PATENT DOCUMENTS

| | | | | |
|---|---|---|---|---|
| 4,837,368 | A * | 6/1989 | Gustafson | B01J 23/60 568/880 |
| 6,452,051 | B1 * | 9/2002 | Eyal | C07C 67/08 560/179 |
| 6,596,521 | B1 * | 7/2003 | Chang | C12P 7/40 435/136 |
| 2005/0124052 | A1 * | 6/2005 | Moore | C07C 51/42 435/138 |
| 2015/0322026 | A1 * | 11/2015 | Stensrud | C12P 7/44 548/554 |
| 2015/0368574 | A1 * | 12/2015 | Stensrud | C07D 307/33 549/326 |

FOREIGN PATENT DOCUMENTS

CA       2657666       *   9/2009

* cited by examiner

*Primary Examiner* — Yevegeny Valenrod
*Assistant Examiner* — Blaine G Doletski
(74) *Attorney, Agent, or Firm* — Vincent T. Kung

(57) ABSTRACT

A process for recovering and using an carboxylic acid derived from a fermentation broth by means of making an ester of the free carboxylic acid and alcohol in carbon dioxide ($CO_2$) without the presence of any other acid catalyst at a reaction temperature and pressure that corresponds to supercritical, critical or near critical conditions for the alcohol and/or $CO_2$ is described. The process can constitute part of a general process of refining carboxylic acids derived from a fermentation broth for use in the production of a variety of chemical compounds, such as $C_4$ platform compounds, polymers, or fuels.

28 Claims, 7 Drawing Sheets

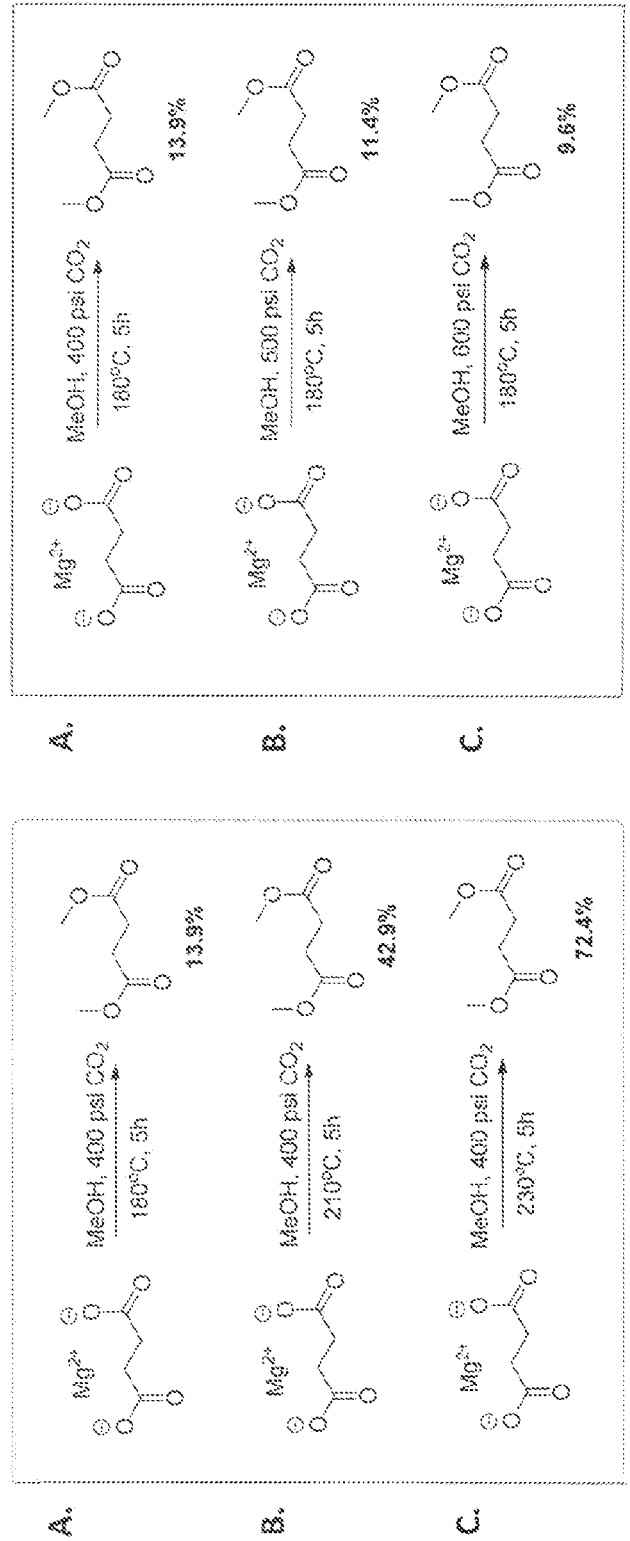
FIG. 6 Temperature Variation
FIG. 7 Pressure Variation
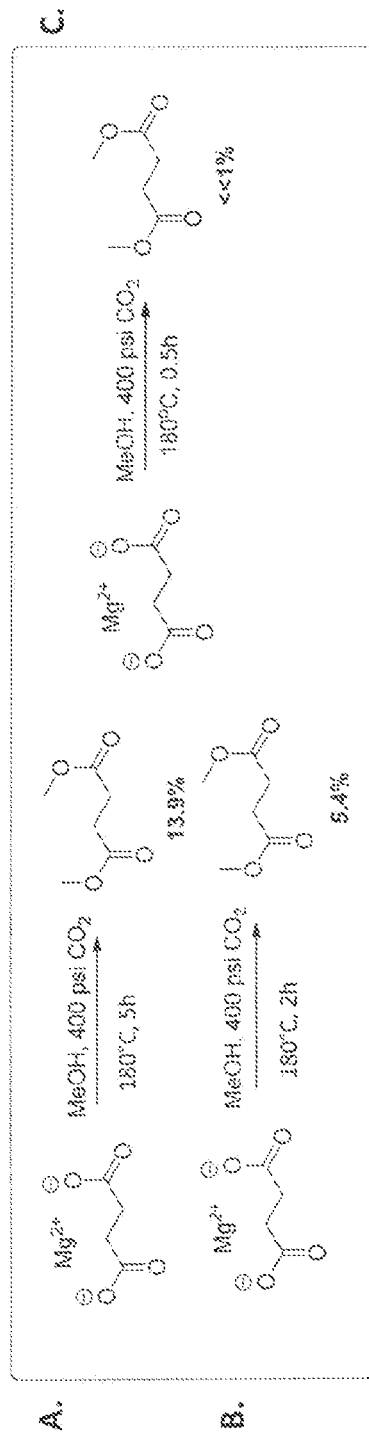
FIG. 8 Variation in Reaction Times

US 9,464,026 B2

RECOVERING AND USING CARBOXYLIC ACIDS FROM A FERMENTATION BROTH

PRIORITY CLAIM

The present Application is a national stage entry of international Application No. PCT/US2013/073783, filed Dec. 9, 2013, which itself claims benefit of priority from U.S. Provisional Patent Application No. 61/739,769, filed Dec. 20, 2012, the contents of which are incorporated herein.

FIELD OF INVENTION

The present invention relates to a process for the production of carboxylic acids. In particular, the invention pertains to a method for recovering carboxylic acids from a fermentation broth.

BACKGROUND

Carboxylic acids, such as the four carbon succinic, malic, maleic and fumaric acids, as well as their derivatives play an important role as precursor molecules for a variety of other chemicals, including the biodegradable polyester resins, dyestuffs, and pharmaceuticals and as additives in the food industry. Currently, for example, succinic acid is largely produced commercially from crude oil by catalytic hydrogenation of maleic anhydride to succinic anhydride and subsequent hydration or by direct catalytic hydrogenation of maleic acid. This traditional way of producing succinic acid from petrochemicals is costly and causes pollution problems. In recent years, many have sought to develop a more cost competitive and environmentally-friendly way of producing succinic acid by means of a biological-based fermentative process. The fermentative production of an important dicarboxylic acid is advantageous not only because renewable substrates are used, but also because the greenhouse gas $CO_2$ is incorporated into succinic acid during fermentation.

For instance, these biologically-derived succinic acid (BDSA) processes seek to produce succinic acid by fermenting glucose from biomass separating and purifying the acid, and then catalytically processing it as a platform chemical to produce, for example, 1,4-butanediol (BDO) and related products, tetrahydrofuran and γ-butyrolactone; N-methyl pyrrolidinone (NMP), 2-pyrrolidines or other chemicals that are used to make a wide assortment of products. Existing domestic markets for such chemicals total almost 1 billion pounds, or more than $1.3 Billion, each year. The BDSA processes also promise to reduce reliance on imported oh and to expand markets for domestic agriculture to more than food sources.

Ordinarily, however, the recovery of dicarboxylic acids from a fermentation broth involves forming insoluble salts of the diacids, typically, insoluble calcium salts. In the case of fermentation by fungi such as *Rhizopus oryzae* or *Asperigillus oryzae*, which preferentially make fumaric and malic acid, respectively, the calcium is typically introduced into the broth in the form of $CaCO_3$, which forms $Ca(HCO_3)_2$ in solution. The bicarbonate is effective to maintain the pH of the broth as the diacid being produced tends to lower the pH. The diacid is recovered as the calcium salt form. The calcium salts of such $C_4$ diacids have a very low solubility in aqueous solutions (typically less than 3 g/liter at room temperature), and are not suitable for many applications for which the free acid is needed, such as chemical conversion to derivative products like butanediol and the like. Therefore, the calcium salt is typically dissolved in sulfuric acid, forming insoluble calcium sulfate, which can readily be separated from the free diacid. Calcium sulfate is a product having few commercial applications, and accordingly is typically discarded as a solid waste in landfills or other solid waste disposal sites.

In an alternative process described for example in WO2010/147920, instead of using calcium carbonate, the pH of the medium for fungi growth was maintained using a magnesium oxygen containing compound, such as MgO, $Mg(OH)_2$, $MgCO_3$, or $Mg(HCO_3)_2$ all of which form the bicarbonate salt in aqueous solution. The use of magnesium rather than calcium was found to enhance production of the acid by fermentation. The fermentation was conducted at a pH of 5-8 and more preferably 6.0-7.0. The pH was maintained by the addition of the magnesium oxygen compound, and $CO_2$ was introduced into the medium in combination with the magnesium oxygen compound to maintain a molar fraction of bicarbonate ($HCO_3^-$) of at least 0.1 and most preferably about 0.3 based on the total moles of $HCO_3^-$, $CO_3^{-2}$, and $CO_2$ in the medium. At the end of the fermentation, the liquid portion of the medium contained a majority of diacid as a soluble magnesium salt, which was separated from a solids portion of the medium containing precipitated salts and other insoluble material. The dissolved acid salt was converted into the free acid form by reducing the pH to below the isoelectric point of the diacid using a mineral acid such as sulfuric acid, and lowering the temperature of the medium to (most preferably) not greater than 5° C., which precipitated the free acid from the solution.

While useful for producing a free acid, the techniques described for using the magnesium salts results are expensive, first because the magnesium oxygen compounds cost considerably more than the analogous calcium compounds but also because the bulk of the magnesium remains in the fermentation medium in the form of the magnesium salt of the inorganic acid, and is not useful for further fermentation or other purposes. Further, the need to lower the temperature of the recovered soluble salts to precipitate the free acid adds additional energy costs.

Although the fermentative production of carboxylic acids, such as malic or succinic acid, has several advantages over petrochemical-based processes, the generation of carboxylic acid salts as just discussed carries significant processing costs because of the difficulties associated with the downstream processing and separation of the acids and their salts. When salts are generated in conventional fermentation processes, an equivalent of base is required for every equivalent of acid to neutralize. The amount of reagent used can increase costs. Further, one needs to remove the counter ions of the salts so as to yield free acids, and one needs to remove and dispose of any resulting waste and by-products. All of these individual operational units contribute to the overall costs of the process.

Recovery of carboxylic acids as salts has a number of associated problems and requires several different steps in post-fermentation, downstream processing to isolate tree acids and to prepare the carboxylic acids for chemical transformation and to convert the raw acids to useful compounds. When salts are generated in conventional fermentation processes, an equivalent of base is required for every equivalent of acid to neutralize. The amount of reagent used can increase costs. Further, one needs to remove the counter ions of the salts so as to yield free acids, and one needs to remove and dispose of any resulting waste and by-products. For instance, calcium salts of $C_4$ diacids have a very low solubility in aqueous broth solutions (typically less than 3 g/liter at room temperature), and are not suitable for many applications for which a free acid species is needed, such as chemical conversion to derivative products. Therefore, the calcium salt is typically dissolved in sulfuric acid, forming insoluble calcium sulfate, which can readily be separated from the free diacid. Calcium sulfate is a product having few commercial applications, and accordingly is typically discarded as a solid waste in landfills or other solid waste disposal sites. All of these individual operational units contribute to the overall costs of the process.

The production costs for the bio-based carboxylic acids have as a result been too high for bio-based production to be cost-competitive with petrochemical production regimes. (See e.g., James McKinlay et al., "Prospects for a Bio-based Succinate Industry," APPL. MICROBIOL. BIOTECHNOL., (2007) 76:727-740; incorporated herein by reference.) For example, with most commercially viable succinate producing microorganisms described in the literature, one needs to neutralize the fermentation broth to maintain an appropriate pH for maximum growth, conversion and productivity. Typically, the pH of the fermentation broth is maintained at or near a pH of 7 by introduction of ammonium hydroxide or other base into the broth, thereby converting the di-acid into the corresponding di-acid salt. About 60% of the total production costs are generated by downstream processing, e.g., the isolation and purification of the product in the fermentation broth.

Over the years, various other approaches have been proposed to isolate the di-acids. These techniques have involved using ultra-filtration, precipitation with calcium hydroxide or ammonia, electrodialysis, liquid-liquid extraction, sorption and ion exchange chromatography. (See, Tarsia Kurzroek et al., "Recovery of Succinic Acid from Fermentation Broth." Review. BIOTECHNOLOGY LETTER, (2010) 32:331-339; incorporated herein by reference.) Alternative approaches that some have proposed include operating a fermentation reactor at low pH, which functionally would be similar to operating the fermentation with minimum level of salts, (See, e.g., Carol A. Roa Engel et al., "*Development of a Low-pH Fermentation Strategy for Fumaric Acid Production by Rhizopus oryzae*," ENZYME AND MICROBIAL TECHNOLOGY, Vol. 48. Issue 1, pp, 39-47, 5 Jan. 2011, incorporated herein by reference.)

For example, FIG. 1 shows a schematic diagram of a known process for extracting organic acids from a fermentation broth. Glucose, corn steep liquor, or other sugars, and $CaCO_3$ are introduced into a fermentation reactor 1 and subjected to microbial fermentation 2. A fermentation broth liquid containing a mixture of organic acids and other by-products 3 is extracted and filtered 4. The broth, is neutralized 5 with a strong acid, such as $H_2SO_4$, which generates $CaSO_4$. The reaction mixture is then filtered 6 to remove ceil mass and the $CaSO_4$ which is waste that cannot be recycled; hence, it is disposed of in landfill or employed for gypsum-using applications. The remaining organic acids, glycerol and other by-products 8 can be recovered and fed back into the fermentation reactor as a carbon source, such as described in U.S. Pat. No. 8,183,022, the content of which is incorporated herein by reference. The products can be separated by various techniques, such as crystallization or ion exchange 9. The organic acids can be purified 10, for example, over a carbon, bed.

An alternative approach some have described involves the synthesis of alkyl monoesters by direct esterification of alkali metal salts of carboxylic acids, such as calcium lactate, sodium acetate, sodium benzoate, and sodium salicylate, using carbon dioxide and an alcohol as a way of making bio-based chemicals in an environmentally friendly manner (see, Prashant P. Barve, et al., "Preparation of Pure Methyl Esters From Corresponding Alkali Metal Salt of Carboxylic Acids Using Carbon Dioxide and Methanol" IND. ENG. CHEM. RES. 15 Sep. 2011). The esterification process, however, has a limited application and do not describe the recovery of polycarboxylic acids.

Although these techniques have had some success, they are not able to provide a direct route by which fermentation-derived dicarboxylic or polycarboxylic acids can be recovered in a simple, cost-efficient process from a fermentation broth. Rather, these fermentation techniques often involve the need to go through several different steps to prepare the carboxylic acids in fermentation broth tor chemical transformation and to convert the raw acids to useful compounds.

To reduce waste and costs associated with generating free carboxylic acids and to improve the recovery yield, a need exists for a better, more direct method of recovering a variety of carboxylic acids, such as malic or succinic acid, and which can provide a successful route to simplify downstream chemical conversions from a biologically-derived feedstock. Such a streamlined, green process would be a welcome innovation.

SUMMARY OF THE INVENTION

The present invention describes, in part, a process for recovering and using carboxylic acids from a fermentation broth by converting a carboxylic acid to one or more of its corresponding esters (i.e., monoester, diester, or triester) in a relatively efficient and cost effective manner. In particular, the present process involves obtaining a fermentation broth, from which cell mass and insoluble compounds have been either removed or not, containing at least one free carboxylic acid, or a mixture of carboxylic acids, or at least one free carboxylic acid and an associated alkali or alkaline earth metal salts of the carboxylic acid (e.g., sodium, potassium, or magnesium salts); drying the raw or clarified fermentation broth containing free carboxylic acid into a powder; and reacting the carboxylic acid in the powder with an alcohol under a $CO_2$ atmosphere in the substantial absence of any other acid catalyst, at a reaction temperature or pressure corresponding to supercritical, critical or near critical conditions tor at least the alcohol or $CO_2$, to synthesize the corresponding ester or esters from the carboxylic acid in the powder. In subsequent steps, the esters can be converted back to their corresponding free acid form. One may recycle the synthesis by-products directly back into the original or a new fermentation broth.

The esterification reaction temperature is between about 150° C. and about 250° C., and the operational reaction pressure is between about 400 psi and about 3,000 psi (gauge). Depending on the desired results, the reaction can be run for about 4 hours, up to about 12 hours.

In another aspect the present invention pertains to a method for esterifying a polycarboxylic acid derived from fermentation. The esterification method involves: providing a solution of one or more free carboxylic acids from a fermentation broth and reacting the free carboxylic acids with an alcohol in a $CO_2$ atmosphere without the presence of any other acid catalyst; and selecting an operational reaction temperature or reaction pressure corresponding to supercritical, critical or near critical conditions for at least the alcohol or $CO_2$ to yield an ester corresponding to the free carboxylic acids. The reaction temperature and pressure conditions preferentially drive the reaction towards the formation of diester molecules over monoester molecules when the carboxylic acid is a polycarboxylic acid. The reaction temperature is between about 150° C. and about 250° C., and the reaction pressure is between about 400 psi and about 3,000 psi. Depending on the desired results, the reaction can be run for up to about 12 hours.

In another aspect, the present invention pertains to a method of processing an agricultural product or biomass. The method includes obtaining carbohydrates from the agricultural product or biomass, fermenting the carbohydrates to produce a fermentation broth, drying the fermentation broth to produce a fermentation broth powder, and transporting the fermentation broth powder to a second processing site. The second processing site can be located nearer to a source of demand for a product derivable from the fermentation broth powder, which can be processed or transformed at the second site to produce a product there from.

Additional, features and advantages of the present methods will be disclosed in the following detailed description. It is understood, that both the foregoing summary and the following detailed description and examples are merely representative of the invention, and are intended to provide an overview for understanding the invention as claimed.

BRIEF DESCRIPTION OF FIGURES

FIG. 6 shows a series of reaction diagrams that summarize variations in temperature for $CO_2$-assisted esterification of free succinic acid derived from fermentation broth.

FIG. 7 shows a series of reaction diagrams that summarize variations in initial operational pressure for $CO_2$-assisted esterification of tree carboxylic acid according to the invention.

FIG. 8 shows a series of reaction diagrams that summarize variations in temperature, and reaction times for $CO_2$-assisted esterification. of fee carboxylic acid according to the invention.

DETAILED DESCRIPTION OF THE INVENTION

Section I—Description

Figure 1:
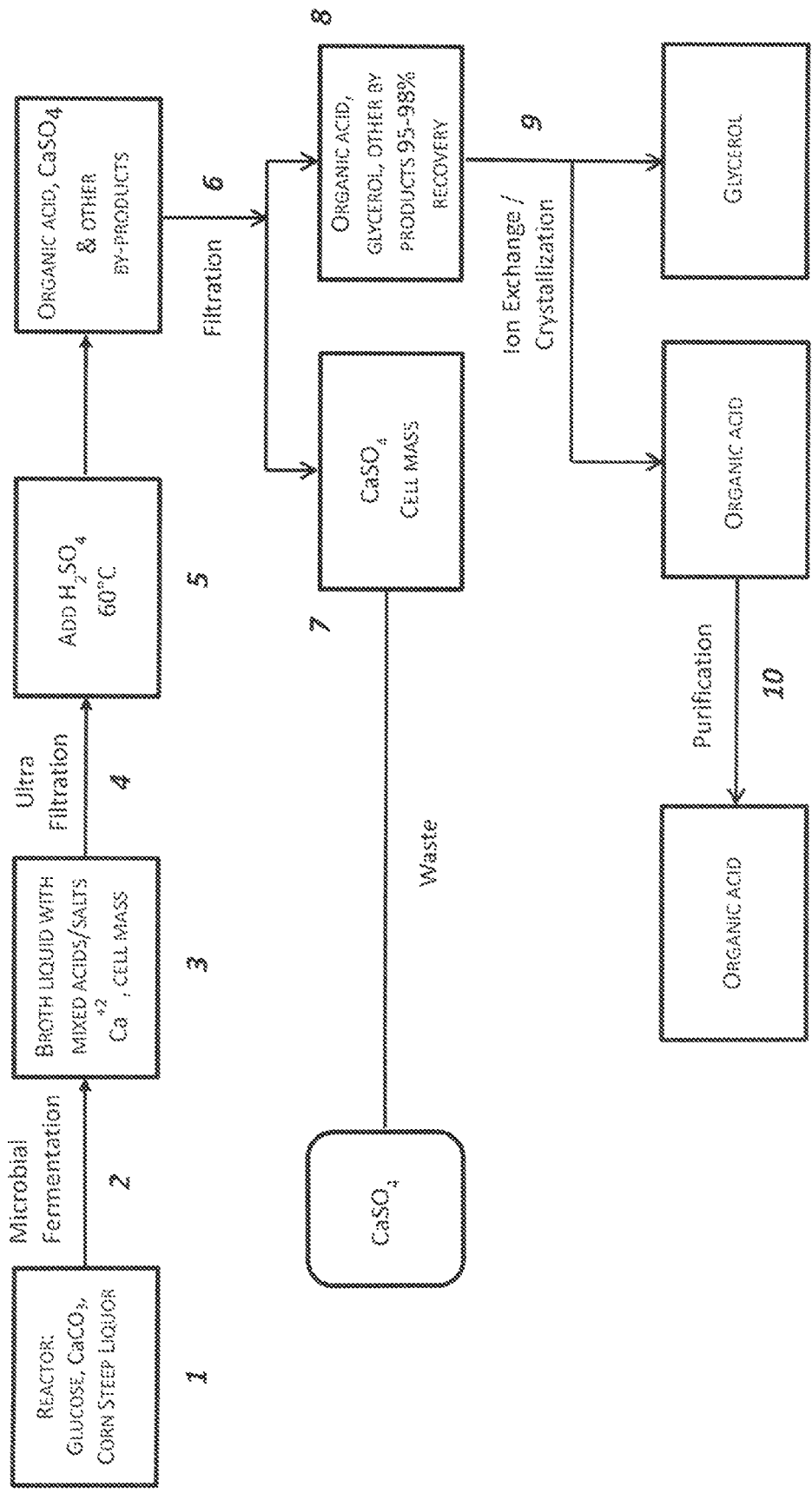
FIG. 1 is a schematic diagram illustrating an extraction of organic acids from a fermentation broth mixture and downstream processing as practiced conventionally.
Figure 2:
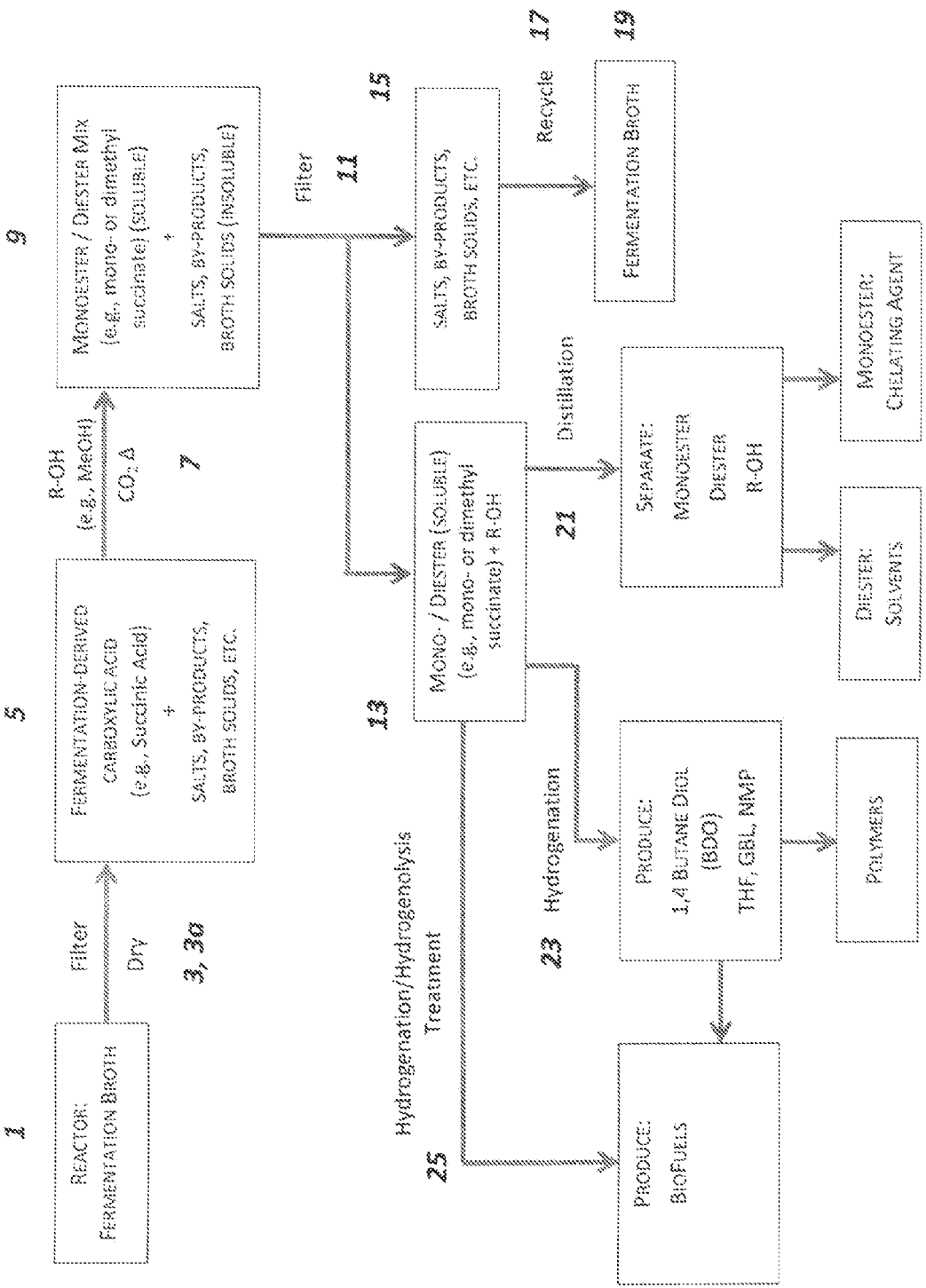
FIG. 2 is a schematic diagram illustrating an iteration of the present process for esterifying an organic carboxylic acid derived from fermentation broth, and further downstream processes that can isolate the resulting esters and/or generate other compounds from such esters.

The present process modifies a conventional, extraction of carboxylic acids-derived from fermentation. As compared to the process shown in FIG. 1, the present approach has several advantages; such as, contrary to convention, one can avoid a need to neutralize the fermentation broth. In another aspect of the present disclosure. FIG. 2 is a schematic representation, showing a general process of extracting carboxylic acids from fermentation broth that includes a version of the present esterification reaction integrated with, further processes that can utilize the resulting esters. As shown, fermentation broth 1 from a reactor is filtered (ultra) 3 to remove biomaterials such as cell mass, and yield carboxylic acids including their salts, by products and other compounds. All of these materials are then dried 3a to make an unrefined mixture 5. This dried mixture of materials is then reacted 7 in a liquid system with an alcohol (R—OH; R=alkyl $C_1$-$C_{12}$) and $CO_2$ at an elevated operational reaction temperature and pressure to yield either monoesters or diesters, or a mixture of both. Only the carboxylic acids react in solution. The resulting mixture 9 is filtered 11 to separate the esters 13 and other by-products 15. The esters are soluble while other by-product compounds are insoluble. The by-products include carbonate salts of calcium, magnesium, or sodium, which can be recovered and recycled 17 back into the fermentation reactor 19. This recycling can lead to significant cost savings and improves the efficiency of the overall fermentation and extraction process. The esters can be processed subsequently either by distillation 21, hydrogenation 23, or hydrogenolysis treatment 25, respectively, to separate the esters, produce $C_4$ platform compounds, such as the hydrogenation products (e.g., BDO, GBL, NMP, etc.), and biofuels (e.g., ethane, ethanol, butane, butanol, propane, propanol, etc.).

As used herein the term "biofuels" refers to a gaseous, liquid, or solid substance that is used as a fuel, which is produced from renewable biological resources such as plant, cellulosic, or agricultural biomass or derivatives thereof. In particular, a biofuel refers to a material that can be used in or as a transportation fuel in internal combustion engines, to power certain machinery, or energy generation applications. For instance, propanol and butanol can be a gasoline additive much the same as ethanol. Butane and propane in liquefied petroleum gas (LPG) and ethane in natural gas can be adapted as fuels in certain transportation systems. Other biologically-derived hydrocarbons, like octanol/octane, or alkanes heavier than $C_5$ or $C_6$ may also be biofuels.

A

The present disclosure describes, in part, a process for recovering and using an carboxylic acid from a fermentation broth. The process includes a method of esterifying free carboxylic acids. As used herein the term "free carboxylic acid" refers to a carboxylic acid compound that is at least 50% in its protonated state when in solution, at or below its pKa value. The present invention involves the discovery of a simple but effective way of producing esters from organic acids that are otherwise costly and difficult to isolate.

The recovery process and esterification method can be applied to producing chemical feedstock molecules from free carboxylic acids derived from a fermentation broth. An advantage of the present invention is that one can use free carboxylic acids directly from a fermentation broth and generate corresponding esters therefrom without the need to isolate or purify the acids from the fermentation broth, as is necessary in conventional extractions from broth. In comparison to certain fermentation processes that neutralize or convert the carboxylic acids to their salts, the present process provides an easier way to isolate and extract carboxylic acids from a fermentation broth. The present process eliminates a need for titration and neutralization of the fermentation broth that can precipitate metal salts, and certain purification steps to produce a stock platform chemical. The free carboxylic acids are converted into esters, which are simpler to process and extract by distillation or other purification techniques without the use of expensive and complicated chromatographic separation columns or resins. For instance in a conventional process, one would need to use ion exchange chromatography to isolate the acids. A small amount of salts may unavoidably carry-over alter the ion exchange. Hence, one may require multiple units of operation to purify the acid to an acceptable quality level. With each added operational unit the costs of the overall process increases. Moreover, in synthesizing the ester of the acid, one can recover the salt as a carbonate or hydroxide, which can be used to regenerate the fermentation broth, and minimize waste. By converting the organic acids to their corresponding esters, we can avoid such issues.

Conventionally, esters are produced when carboxylic acids are heated with alcohols in the presence of an acid catalyst. The mechanism for the formation of an ester from an acid and an alcohol are the reverse of the steps for the acid-catalyzed hydrolysis of an ester. The reaction can go in either direction depending on the conditions used. In a typical esterification process, a carboxylic acid does not react with an alcohol unless a strong acid is used as a catalyst. The catalyst is usually concentrated sulfuric acid or hydrogen chloride. Protonation makes the carbonyl group more electrophilic and enables it to react with the alcohol, which is a weak nucleophile.

In general terms, the present esterification method involves a reaction of fermentation-derived, free organic carboxylic acid with an alcohol in a carbon dioxide ($CO_2$)-predominant atmosphere in substantial absence of any other acid catalyst to produce esters. The esterification reaction is performed in solution under conditions that are either at supercritical., critical or near critical, temperatures and/or pressures for at least one of the alcohol or $CO_2$. Under such conditions, we believe that $CO_2$ self-generates or functions in situ as an acid, catalyst, and regenerates back after the esterification reaction is completed. It is believed that a reactive intermediate (monoalkylcarbornic acid) is being made in situ in large enough quantities to drive esterification and affect ester production. This intermediate, having a similar pKa (e.g.~4-5) as the free carboxylic acid, functions as a carbonic acid, which is much weaker than the usual strong acids. The observed trend of greater ester conversion at higher temperatures adduces a relatively large energy of activation for this process. As used herein, the term "substantial absence" refers to a condition in which an acid catalyst is either largely or completely absent, or is present in de minimis or trace amount of less than catalytic efficacy. In other words, no other acid catalyst is present, or is present at a level less than 10%, 5%, 3%, or 1% weight/weight relative to the carboxylic acid in the reaction.

An advantageous feature of the inventive process is that activation of the free carboxylic acid as an acyl halide (e.g., fluoride, chloride, bromide) or by using strong mineral acids is unnecessary. Acyl halides are inconvenient to use because these species are inherently reactive, have issues with stability, waste treatment, and can be cumbersome and costly to make.

In the present, process, carbon dioxide functioning as a catalyst instead of the usual strong acids removes the need to introduce a strong acid into the esterification reaction. This feature can circumvent the usual need to adjust pH values in order to remove the catalyzing acid, enabling a simpler and cleaner synthesis. One can simply proceed to filter the resultant product to remove alkali or alkaline earth metal carbonate or other salts. A cleaner product will save costs in purification and downstream processing for conversion to other chemical feedstock.

The process described herein is a more environmentally benign way of producing esters. As it is believed that the carbon dioxide can self-generate an acid catalyst in situ in the presence of the alcohol during the esterification reaction, the present method does not require the use or addition of another acid catalyst species. In other words, the reaction kinetics with $CO_2$ alone can drive the esterification in the substantial absence of any other acid catalyst. To reiterate, the present process does not require activation of free acids as, for example, an acyl chloride or by strong acids (i.e., Fischer esterification).

In general, the esterification is conducted at an operational or reaction temperature between about 150° C. to about 250° C., at a reaction pressure of between about 400 psi and 2,500 psi or 3,000 psi (gauge), for an extended period, such as about 4 hours, up to about 12 hours. Typically, the temperature can be in a range between about 170° C. or 190° C. to about 230° C. or 245° C. (e.g., 175° C., 187° C., 195° C. or 215° C.), and the operational pressure is between about 900 psi or 950 psi and about 2,200 psi or 2,400 psi (e.g., 960 psi, 980 psi, 1020 psi or 1050 psi). Alternatively, the temperature can be in a range between about 180° C. to about 245° C. (e.g., about 185° C. or 200° C. or 210° C. to about 220° C. or 235° C. or 240° C.), and the operational pressure is between about 1000 psi and 2,350 psi (e.g., 1,100 psi, 1,200 psi, 1,550 psi, 1,750 psi, 1,810 psi, or 1,900 psi). Other temperatures may be within a range, for example, from about 160° C. or 1.85° C. to about 210° C. or 225° C., and other operational pressures may be within a range, for example, from about 1,150 psi or 1,500 psi to about 1,800 psi or 2,000 psi.

These reaction temperatures and pressures correspond to supercritical, critical or near critical conditions for the alcohol(s) or $CO_2$. Table 1 lists, for purpose of illustration, critical parameters for some common solvents (i.e., methanol, ethanol, 1-propanol, 1-butanol, water, and $CO_2$).

TABLE 1

Critical Data for Select Substances (Yaws, C. L., Chemical Properties Handbook, In McGraw-Hill: 1999; pp 1-29.)

| Substance Name | Molecular Weight | Critical Temp. (K)/° C. | Critical Pressure (bar)/psi | Critical Density (g/cm$^3$) |
|---|---|---|---|---|
| Methanol | 32.042 | 512.58/239.43 | 80.96/1174.226 | 0.2720 |
| Ethanol | 46.069 | 516.25/243.10 | 63.84/925.920 | 0.2760 |
| 1-Propanol | 60.095 | 537.4/264.25 | 51.02/739.983 | 0.2754 |
| 1-Butanol | 74.122 | 563.0 ± 0.3/ 289.85 | 45.0 ± 4.0/652.671 | 0.3710 |
| Water | 18.015 | 647.13/373.98 | 220.55/3198.807 | 0.3220 |
| Carbon dioxide | 44.010 | 304.19/31.04 | 73.82/1070.669 | 0.4682 |

At conditions above the critical point (i.e., critical temperature and pressure), the fluid exists in a supercritical phase where it exhibits properties that are in between those of a liquid and a gas. More specifically, supercritical fluids (SCFs) have a liquid-like density and gas-like transport properties (i.e., diffusivity and viscosity). This can be seen in Table 2,wherein the typical values of these properties are compared between the three fluid types—conventional liquids, supercritical fluids, and gases.

TABLE 2

Comparison of Typical Physical Property Values of Liquids, Supercritical Fluids, and Gases.

| Property | Liquid | SCF | Gas |
|---|---|---|---|
| Density (g/mL) | 1 | 0.3 | $10^{-3}$ |
| Diffusivity (cm2/s) | $5 \times 10^{-6}$ | $10^{-3}$ | 0.1 |
| Viscosity (Pa · s) | $10^{-3}$ | $10^{-4}$ | $10^{-5}$ |

Likewise, "near critical" refers to the conditions at which either the temperature or pressure of at least the alcohol species or $CO_2$ gas is below but within 150K (e.g., within 50-100K) or 220 psi (e.g., within 30-150 psi) of their respective critical points. It is believed that as temperatures and pressures reach near critical, critical or supercritical conditions, the solubility of the reagents are enhanced, which promotes the esterification reaction. In other words, the $CO_2$ gas, alcohol, and acid species are better able to interact under near critical, critical or supercritical conditions than under less rigorous conditions. The reaction does not require that, both the alcohol species and $CO_2$ gas be at near-critical, critical or supercritical conditions; rather, the reaction is operative as long as either one of the species satisfies such a condition.

If the present esterification reactions are operated at higher temperatures and greater pressures, up 10 about 250° C. and about 3,000 psi (gauge), respectively, for reaction times of up to about 10 or 12 hours, one can produce significant amounts of ester product at relatively greater selectivity and level of purity within a shorter reaction time than before, which was about 18-20 hours. At lower operational temperatures (<190° C.), formation of monoester molecules of polycarboxylic acids is more prevalent, while reactions at temperatures≥190° C. or 195° C., will convert preferentially the polycarboxylic acids to diesters. By selecting a temperature in a higher range from about 190° C. or 195° C. or 200° C. to about 245° C. or 250° C., one can preferentially drive the reaction to a greater rate of diester conversion. The esterification can yield a minimum of about 50%, desirably about 65% or 70%, of a diester of the carboxylic acid. Reactions that are performed at or near supercritical operating conditions tend to produce better results. When operated at or near critical conditions of about 230° C. or about 240° C. for methanol and about 31° C./1000 psi for $CO_2$, one is able to achieve conversions rates of about 90% or better, typically about 93% or 95%. One can achieve greater yields by adjusting the permutations of different combinations of temperature and reaction times (e.g., higher temperatures and shorter reaction times (e.g., less than 10 or 12 hours, between 4 and 8 hours) or vice versa), which can be an advantage over current approaches. With optimization, esterification conducted at 250° C. under either the same or greater $CO_2$ pressure, the yield would be nearly quantitative (i.e., ≥95% yield), for example, up to about 98%, 99%, or 99.9% conversion.

As the accompanying Examples will show, variation in reaction conditions suggests that one can generate more diester product with higher temperatures and/or protracted reaction times. As stated before, however, different permutations in temperature can influence the duration of the esterification reactions to produce the same amount of ester product. The reactions according to the present method are not conducive to a significant degree of side product formation; hence one can avoid cyclization of the carboxylic acids and other starting reagents. Potential dangers of decarboxylation at high temperatures (i.e., >145° C. or >150° C.) are not observed in the present method.

Using an amount of the alcohol solvent in excess of the carboxylic acid, one can produce a very clean esterification. The present synthesis process produces very clean ester products at about 70%-72% initial purity, without generation of significant amounts of side products such as low molecular weight acids—acetic or formic acid—molecular rearrangements or cyclic products, which one could normally find in standard acid catalyzed, esterification at high temperatures. The esters can be refined to achieve about 90-98% purity. The purification can be accomplished, for Instance, by means of crystallization, chromatography, or distillation.

Typically, the resulting ester products can be either monoesters or diesters, or form a mixture of both. One can control the reaction to drive the esterification toward either one ester form or another. For instance, one may select an operational, temperature and pressure that preferentially drives the esterification reaction towards formation of diester molecules. Likewise, one can control, whether esters are formed from either a single carboxylic acid species (e.g., succinic acid) or a mixture of multiple different kinds carboxylic acids (e.g., acetic, citric, lactic, malic, maleic, succinic acids) that may be present and derivable from fermentation broth. In other words, one can use a variety of different kinds of carboxylic acids in accord with the present esterification reaction to produce a variety of different esters. These esters, in turn, can be isolated, further modified in downstream chemical processes and converted, in certain embodiments, into useful compounds such as for pharmaceutical, cosmetic, food or feed ingredient, polymer materials or biofuels. For instance, succinic esters can be converted into a polymer, such as polybutylene succinate (PBS).

In the present esterification process, both the catalyst ($CO_2$) and the esterification reagent (alcohol) are present in large excess relative to the amount of free carboxylic acid. $CO_2$ should be in the gas phase during the reaction phase, regardless of its origin (e.g., gas tank or dry ice), as the reaction is conducted at high temperatures. Addition of solid $CO_2$ is strategic in the case where sealed pressure reactors are used, in that it allows for slow sublimation of gaseous $CO_2$ formation as the reaction apparatus is being assembled. This can minimize $CO_2$ loss. In a $CO_2$ (i.e., $CO_2$-containing) atmosphere, the concentration of $CO_2$ in the reaction atmosphere can be at least 10% or 15% by volume, favorably about 25% or 30%, preferably greater than 50%. For better reaction results, the concentration of $CO_2$ should be maximized. Desirable concentrations of $CO_2$ are from about 75% or 80% to about 99.9% by volume, typically between about 85% and about 98%. Nitrogen ($N_2$) gas or air is permissible in the reactor, but preferably the concentration of gases other than $CO_2$ is kept at either a minor percentage (<50%) or de minimis amount.

Any liquid alcohol with an R-group of $C_1$-$C_{20}$ can serve as the solvent reagent or first alcohol species. The R-group can be saturated, unsaturated, or aromatic. A mixture of different kinds of alcohols (e.g., $C_1$-$C_{12}$) can also be used in the reaction, but will produce a corresponding mixture of different esters depending on the particular R-group. Certain lower alcohol species with $C_1$-$C_6$ alkyl groups are preferred as the reagent in the first esterification with $CO_2$ in view of their common availability, inexpensiveness, and mechanistic simplicity in the esterification reaction, further, alcohols such as methanol, ethanol, propanol, or butanol are preferred because of parameters such as their comparatively simple structure and that the reactions are more easily controlled with respect to the supercritical, critical or near critical temperatures and pressures of these alcohol species. Alternatively, in some embodiments, the alcohol can also be a $C_2$-$C_6$-diol. Esterification with a diol can generate monomers or low molecular weight oligomers that can be readily polymerized.

One can use a variety of different carboxylic acids, for example, selected from: a) monocarboxylic acids: formic acid, acetic acid, propionic acid, lactic acid, butyric acid, isobutyric acid, valeric acid, hexanoic acid, heptanoic acid, decanoic acid, lauric acid, myristic acid, and $C_{15}$-$C_{18}$ fatty acids; b) dicarboxylic acids: fumaric acid, itaconic acid, malic acid, succinic acid, maleic acid, malonic acid, glutaric acid, glucaric acid, oxalic acid, adipic acid, pimelic acid, suberic acid, azelaic acid, sebacic acid, dodecanedioic acid, glutaconic acid, ortho-phthalic acid, isophthalic acid, terephthalic acid; or c) tricarboxylic acids: citric acid, iso-citric acid, aconitic acid, tricarballylic acid, and trimesic acid. The carboxylic acids can include a mix of associated alkali or alkaline earth metal (e.g., sodium, potassium, or magnesium) salts of these carboxylic acids. Desirably, the acid is a dicarboyxlic or tricarboxylic acid.

B

The present esterification process can be integrated into fermentation-based production of carbon chain feedstocks and to provide a more convenient method of generating esters from carboxylic acids derived from a renewable source. The process cars reduce the amount of waste by means of recycling of by-products back into the fermentation broth, either in a continuous or batch process. We have also found that in the present esterification process, when free carboxylic acid is reacted with an alcohol and $CO_2$ absent any other acid catalyst, the free protonated form of the carboxylic acids has greater solubility in the alcohol solvent than their corresponding salts. Performed under similar reaction conditions, the esterification reaction using the free carboxylic acid as a reagent will yield about 2-3 times greater amount of ester product than, the reaction that uses the salt species as a reagent. This result can be seen when one compares the reaction of accompanying FIG. 4B (free acid) with that of FIG. 6A (acid salt), and in Table 4, Examples 2 and 3 (acid salt), with Examples 5 and 6 (free acid), respectively. It is believed that solubility is a factor for the difference. For instance, since the solubility of magnesium salts in methanol and ethanol are significantly better than that of calcium salts, product yield from a reaction of a calcium salt is much lower man that produced from a starting reagent of a corresponding magnesium salt.

Through the distillation process one can concentrate the esters by driving off the alcohol, and then filter the by-products resultant from ester synthesis. Further distillation of a mixed-acid ester product mixture according to the boiling points of the different ester species, permits one to separate the various individual esters. For instance. Table 3 provides boiling points for a sample of common, esters that may be present in an ester product mixture according to the present invention.

TABLE 3

Boiling Points for Some Common Esters

| Ester Species | Boiling Point (° C.) | Ester Species | Boiling Point (° C.) |
|---|---|---|---|
| methyl-acetate | 56.9 | ethyl-acetate | 77.1 |
| methyl-formate | 32 | ethyl-formate | 54.0 |
| methyl-lactate | 145 | ethyl-lactate | 151-155 |
| dimethyl-malate | 104-108 (1 mmHg) | diethyl-malate | 281.6 |
| dimethyl-succinate | 200 | diethyl-succinate | 217-218 |
| trimethyl-citrate | 176 (16 mmHg) | triethyl-citrate | 235 (150 mmHg) |

After recovering the esters in the remaining solution, the materials are in a readily usable form and one can either distill the ester mixture to separate the different ester species and any remaining alcohol Once the esters are recovered, one can use the monoesters as precursors for conversion into chelating agents, and the diesters as solvents.

An advantage of recovering the carboxylic acids from fermentation in the form of their corresponding esters is that downstream processing of the esters is less energy intensive than the hydrogenation of the free acids. Another advantage of the present esterification process is that, one will find the present process simpler and easier, as compared to other approaches, to refine carboxylic acids for $C_4$ chemical platforms from fermentation. It simplifies efforts to separate esters from the other insoluble materials, as well as minimizes the amount of salt that one needs to separate. In an integrated process enables one to directly esterify a combination of free acid and salts that is produced in a low-pH fermentation, in which, the fermentation is operated at a pH of less than, the pKa of the carboxylic acids. The process can be less energy intensive that current recovery approaches.

Figure 3:
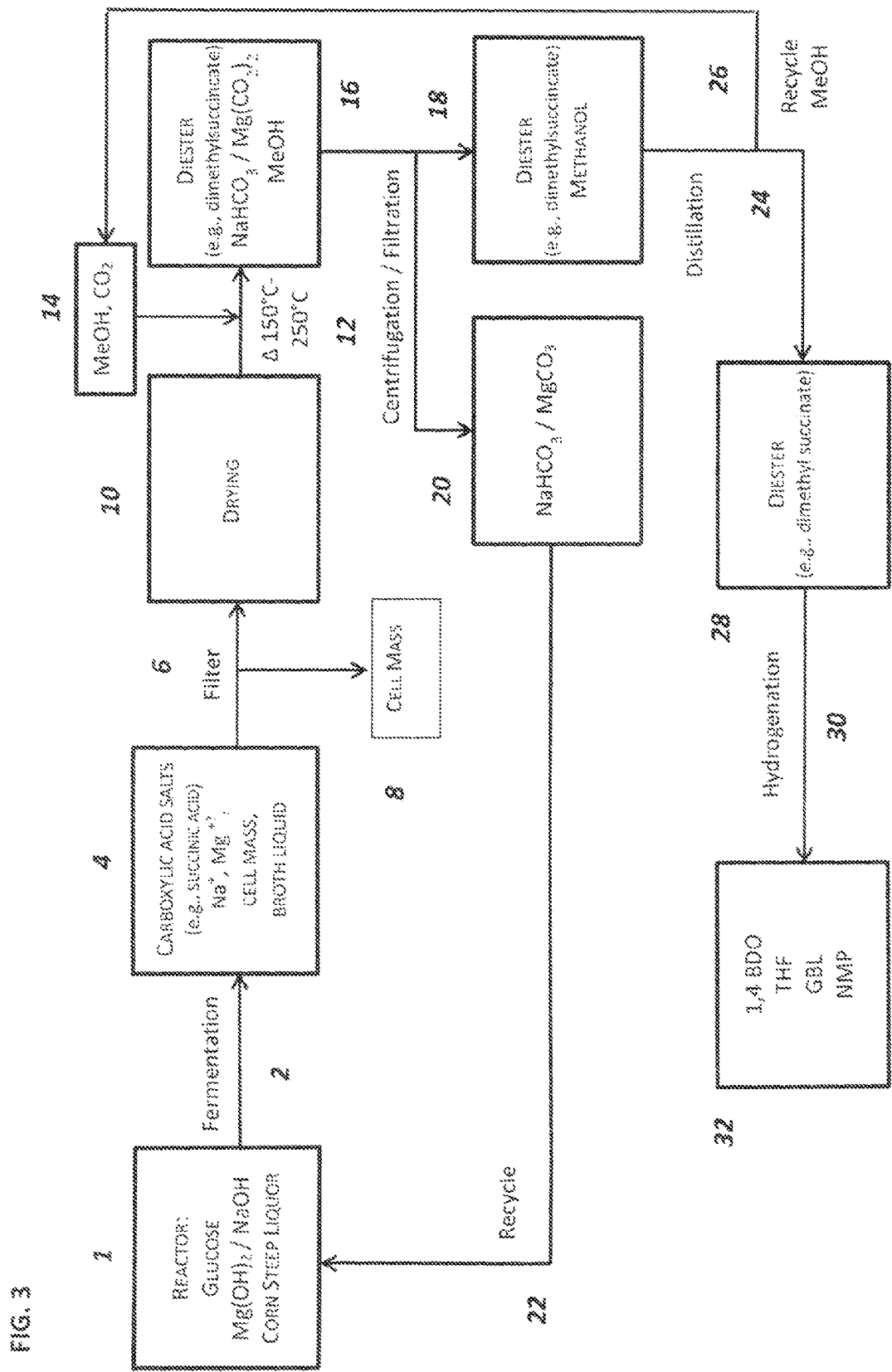
FIG. 3 is a schematic diagram showing an example of ester production using succinic acid derived from fermentation, and a downstream process in which Na and Mg salts are recycled back into the fermentation reactor, in accordance with another embodiment of the present process.

We will now expound in more detail the concepts of the general process depicted in FIG. 2. FIG. 3 shows a schematic diagram of a downstream processing that incorporates an iteration of the present esterification process, in particular, FIG. 3 depicts an example of using succinic acid or any other kind of carboxylic acid derived from a fermentation broth is extracted and reacted with an alcohol in the presence of excess $CO_2$ to generate esters. According to this iteration of the process, glucose, corn steep liquor, or other sugars, and $Mg(OH)_2$/NaOH are introduced into a fermentation reactor 1 and fermented 2 to produce succinic acid and. its sodium or magnesium salt. A fermentation broth liquid containing a mixture of carboxylic acids, salts, and other by-products 4 is filtered 6 to remove cell mass 8 and other insoluble matter. The fermentation is performed at a low pH value, in which one starts at a higher pH (e.g., pH ~7 or 8) and during the course of the fermentation, the pH value drops to about 2-3. One will produce a mixture of salts and free acid present, for example, in a ratio range of about 9:1 w/w to 7:3 w/w of salt to acid. The fermentation broth is retrieved from a fermentation reactor at a pH value of less than the pKa of the carboxylic acids, (e.g., pH 5). Typically, the fermentation broth is at a pH value in a range between about 1.5 and about 4.5.

The broth extract is then dried 8 to a powder. When drying the mixed acid filtrate should remove as much, water as possible. The drying step can be accomplished, for instance, by means of spray drying, drum drying, or cryodesiccation. As with esterification in general, relatively low water content is desired, otherwise the reversible reaction will tend to hydrolyze back to the dicarboxylic acid, in the present process, a maximum residual moisture content of about 5% by weight should be maintained. One would expect an increase in ester yield of up to about 98 or 99% with samples that contain less than 3% wt. of water.

The dried powder (average moisture content between about 1 wt. % and 5 wt. %, desirably ≤3 wt. %) is then reacted 12 with an alcohol 14 which serves as an alkylating agent, in excess $CO_2$ at a temperature between about 180° C. to about. 250° C. for a duration of about 4 hours or more to esterify the carboxylic acids. In this example, succinic acid is reacted in methanol and $CO_2$ to generate dimethyl succinate. Along with the free carboxylic acid, any remaining free amino acids which were in the fermentation broth are also esterified.

One can also produce various precursor chemicals by subjecting the ester mixture to hydrogenation. One can produce a variety of compounds, including for example: 1,4-butane-diol (BDO), tetrahydrofuran (THF), γ-butyrolactone (GBL), or N-Methyl-2-pyrrolidone (NMP), which in turn can be farther modified to other useful compounds, by means of hydrogenation processes such as described in U.S. Pat. No. 4,584,419A (relating to process for the production of 1,4-butane-diol involving the hydrogenation of a di($C_1$ to $C_3$ alkyl) ester of a $C_4$ dicarboxylic acid); UK Patent Application No. GB2207914A (relating to a process for production of a mixture of butane 1,4-diol, γ-butyrolactone, and tetrahydrofuran from maleate and fumerate); International Patent Application Nos. WO8800937A (relating to a process for the co-production of butane-1,4-diol and γ-butyrolactone by means of hydrogenation of dialkyl maleate) or WO 82/03854 (relating to a process for hydrogenolysis of a carboxylic acid ester), the content of each of the preceding patent disclosures is incorporated herein in its entirety by reference.

As the example illustrates in FIG. 3, when reacted with methanol in accord with the reaction temperatures and pressure parameters defined above, succinic acid esterified to produce dimethyl succinate (as predominant product), $NaHCO_3$, $MgCO_3/Mg(HCO_3)_2$ and excess methanol 16. The dimethyl succinate and methanol 18 are separated from $NaHCO_3$ and $MgCO_3$ 20. The carbonates, unlike $CaSO_4$, can be recycled 22 back, into the reactor 1, either for a continuous process or in a fresh batch process. The dimethyl succinate and methanol are further separated 24 from each other with the methanol 7 being recycled 26. Subsequently, the dimethyl, succinate 28 can be hydrogenated 30 into a variety of different chemical products 52, including for instance 1,4-butane-ldiol (BDO), tetrahydrofuran (THF), γ-butyrolactone (GBL), or N-methyl-2-pyrrolidone (NMP).

Another advantage of the present process is that it can simplify the transport and processing of crops for fermentation products. For instance, with a dried fermentation broth powder one is freed from issues associated with working with wet or liquid stock. A dried fermentation broth powder can be more economically shipped, to a location different from where the fermentation broth is made or sourced. This will enable the reaction, for ester synthesis to be performed at a remote location different from where the fermentation broth is sourced, and expand the geography of where the final processing facilities can be situated.

Hence, we also envision that the esterification process described herein can be integrated into a method for processing an agricultural product or biomass. The method involves obtaining carbohydrates from the agricultural product or biomass, fermenting the carbohydrates to produce a fermentation broth, drying the fermentation broth to produce a fermentation broth powder, and transporting the fermentation broth powder to a second processing site. This second site can be located closer to a source of demand for a product derivable from the broth powder, which can be esterified and/or otherwise processed at the second site to produce a product therefrom.

Section II—Examples

Examples prepared according to the present esterification method are integrated into a process for isolating free carboxylic acid from a fermentation broth. The method involves generally the following steps: a) filtering a crude fermentation broth to remove ceil mass and. other biological debris from a fermentation broth; b) desiccating the fermentation broth: c) reacting the dried fermentation broth with an excess of methanol ($CH_3OH$) or ethanol ($C_2H_5OH$) and carbon dioxide ($CO_2$) at a temperature about 150° C. up to the near critical or critical temperature and under near critical or critical pressure of the alcohol and/or $CO_2$ reagents, to produce a mixture of monoesters and diesters and carbonate ($NaHCO_3/MgCO_3$); d) filtering the reaction product to remove by-products; and e) purifying by distilling, the esters.

The fermentation broth filtrate was dried, to remove all or nearly all of the water to produce a powder of mixed organics. Using a spray dryer or drum dryer, one aerosolizes the raw solution containing mixed carboxylic acids to desiccate into a powder. The desiccated powder is suspended in an alcohol solvent. The powder reacts with the alcohol according to the conditions described herein to esterify into either monoesters or diesters.

Each of the following examples was performed according to the following general protocol, except for variations in reaction temperature, pressure, time, and/or acid species as indicated, *mutatis mutandis*. Ten grams of freeze-dried succinic acid fermentation broth (off-white powder) and 300 g of methanol, were charged to a 1L stainless steel vessel, jacketed, and fixed to a Parr reactor. While stirring mechanically at 1100 rpm, the internal headspace of the reactor vessel was purged with $N_2$ and then pressurized initially to 400 psi with $CO_2$ and heated to 180° C. for 5 hours. The internal pressure was observed to be ~1650 psi at 180° C. After the reaction time, the reactor body was cooled in a water bath, until reaching room temperature and pressure released. The heterogeneous mixture was then tittered and solids were dried overnight under vacuum. Samples of the solid material and the solution were analysis quantitatively using gas-chromatography/mass spectrometry (GC/MS). The yield of dimethyl succinate was determined to be 31.9% with more than 95% of the available magnesium succinate consumed in the reaction. The remaining balance of product included the corresponding monoesters as the greater part, and was in a range of about 60% to about 65%.

As the reactions depicted in the accompanying figures and tables show, modification and selection of certain temperature and pressure parameters causes reactions to yield preferentially more of the diester compounds. In certain examples of the present process, the esterification reactions yielded snore than 50%, typically more than 70% or 80% di-akyl succinate or esterification. As stated before, the unreached materials and the undesired products are recycled into the fermentation reactor. Subsequent separation, of the mono-esters and di-esters was achieved by crystallization.

Figure 4:
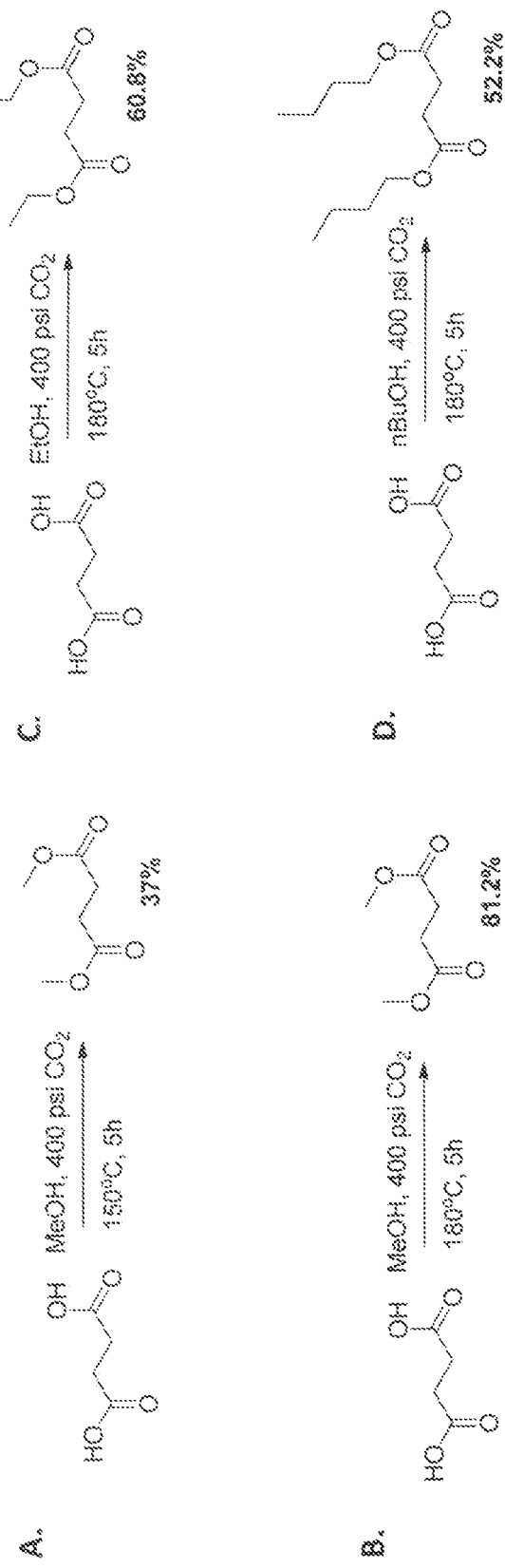
FIG. 4 is a diagram, that illustrates $CO_2$-assisted esterification of free succinic acid in various alcohols that are converted to corresponding dimethyl, diethyl, or dibutyl esters, according to the present invention.

FIG. 4 shows a series of esterification reactions which summarize $CO_2$-assisted esterification of free succinic acid in various alcohols. FIG. 4A shows succinic acid reacted with methanol in 400 psi $CO_2$ gas, at 150° C. for 5 hours, which achieved a yield of about 37% dimethyl succinate. When the operational temperature was increased to 180° C. in the reaction of FIG. 4B and all other parameters kept the same as in FIG. 4A, the amount of dimethyl succinate yield increases more than, two-fold to about 81.2%, FIG. 4C represents free succinic acid reaction at 180° C. under present operational conditions in ethanol, which generates diethyl succinate in good yield of about 60.8%. In FIG. 4D, tree succinic acid was reacted at 180° C. under operational conditions in n-butanol, which generates dibutyl succinate at about 52.2% yield. These examples demonstrate the versatility of the present esterification reaction in view of different kinds of alcohols.

Figure 5:
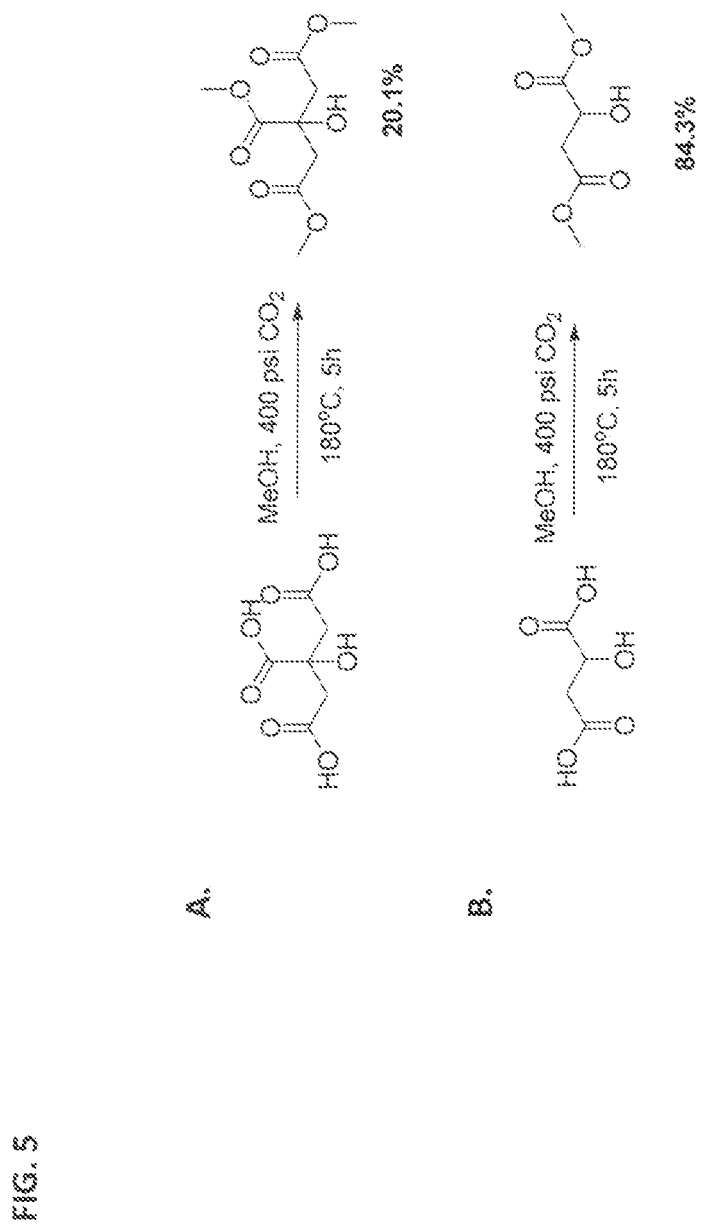
FIG. 5 is a diagram that Illustrates $CO_2$-assisted esterification of other polycarboxylic acids.

FIG. 5 shows examples of $CO_2$-assisted esterification of other kinds of carboxylic polyacids. In FIGS. 5A and 5B, succinic acid was substituted respectively with citric acid, a tri-carboxylic acid, and malic acid. The yield of trimethyl-citrate was reasonable at about 20.1%, demonstrating that the $CO_2$-assisted protocol can be applied to tricarboxylic acids. The yield of the dimethyl analogue of malic acid was good at about 84.3%. Hence, the new method of esterification is feasible for general use with other acids.

Table 4 summarizes results of several reactions that were performed according to the esterification method of the present disclosure as depicted in. FIGS. 6, 7, and 8. Each set of examples is arranged in terms of a variation of an operational condition under which the reaction, was performed: A) temperature, B) pressure, and C) reaction time. In each of the examples, succinic acid from a fermentation broth is used as the substrate. The filtered clarified broth containing free acid and salts are dried and later reacted with methanol and $CO_2$ in solution. (As the reactions are heated, the actual operational temperatures and pressures within the reactor vessel will exceed the initial temperatures and pressures provided herein.)

In the three examples of Set A, we carried out the reaction for 5 hours at an initial $CO_2$ pressure of 400 psi, under different temperatures: Ex. A-1 at 180° C. Ex. A-2 at 210° C., and Ex, A-3 at 230° C. The percent conversion of acid to its corresponding diester increased with higher operational temperature. FIG. 6 shows the effect of varying temperature in a series of esterification reactions of succinic acid and its salt. In FIG. 6A, the esterification of succinic acid is performed at a temperature of about 180° C., over a period of 5 hours. The reaction produced about 13.9% yield of dimethyl succinate. FIG. 6B shows the same reaction as in FIG. 6A, when the reaction time held constant, but with the temperature raised to about 210° C., which yields about 42.9%. FIG. 6C shows a reaction at 230° C. and yields about 72.4%. This suggests that as the temperature increases, the reaction, kinetics drives toward, a more complete reaction of the acid and alkylating agent, and a greater yield of the dialkyl-ester. Reactions performed at or near critical temperature and/or pressure conditions can produce about 95%, likely≥97% or 98%, conversion.

In Set B and FIG. 7, we performed the esterification reaction for 5 hours at an initial temperature of 180° C., and varied the initial $CO_2$ gas pressures: Ex. B-1 at 400 psi, Ex. B-2 at 500 psi, and Ex. B-3 at 600 psi. The percent conversion of acid to its corresponding diester was moderate, and the amount yield did not show significant difference statistically, The initial $CO_2$ gas pressure in the reactor did not exert much effect in conversion of the acid to its diester, but the operational, pressures in the reactor during the reaction suggest an effect on yields.

In Set C and FIG. 8, we performed the esterification reaction at a constant pressure and temperature but varied the duration of the reaction. Ex. C-1 at 5 hours, Ex. C-2 at 2 hours, and Ex. C-3 at 0.5 hours. The examples shown in FIG. 8 suggest that a greater amount of diester was converted from the acid with increased reaction time.

Figure 9:
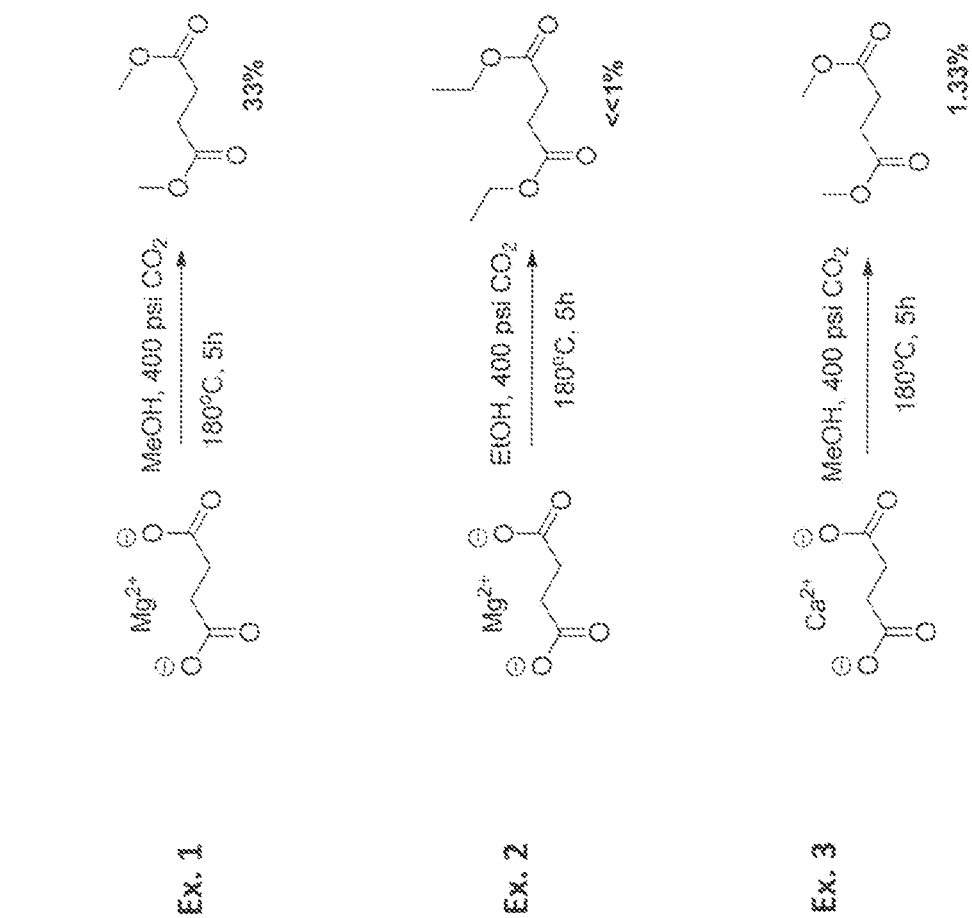
FIG. 9 shows a series of reaction diagrams that summarize the reaction results of succinic acids and their $Mg^{2+}$ and $Ca^{2+}$ salts.

FIG. 9 shows a first set of $CO_2$-assisted esterification reactions using a concentration of succinate salts of about 4% w/w, which are presented as Examples 1-3 in Table 5. In Examples 1 and 2, succinic acid and its magnesium ($Mg^{2+}$) salt was reacted in methanol and ethanol at 210° C. and 180° C., respectively., for a reaction time of 5 hours. The reactions produced about 33% dimethyl succinate and about 1% diethyl succinate, respectively. Methanol exhibits a greater capacity to dissolve the succinate salt than ethanol. Magnesium succinate exhibits a reasonable level of solubility in methanol, while it exhibits limited solubility in ethanol, even at high temperatures. Hence, the yield of diethylsuccinate was negligible. Example 3 shows a reaction using calcium ($Ca^{2+}$) succinate, at 180° C., over 5 hours. The reaction yields only about 1.33% of the corresponding dimethylsuccinate. Relatively low conversion rates in Examples 2 and 3, also highlights the solubility difference between corresponding alkali earth salts. The calcium succinate salt is insoluble in methanol, even at high temperatures. The methanol to salt molar ratio used in the $CO_2$ experiments was approximately 110:1 for methanol to magnesium succinate. Likewise, the ratio was about 100:1. for methanol to the other carboxylic acids.

TABLE 4

Variations in Reaction Conditions

| Example | Substrate | Alcohol | Reaction Time (h) | Temperature (° C.) | Initial $CO_2$ pressure (psi) | % Conversion to Diester | |
|---|---|---|---|---|---|---|---|
| A | | | | | | | |
| 1 | Succinic acid fermentation broth, $Mg^{2+}$ salt | Methanol | 5 | 180 | 400 | 13.9 | |
| 2 | Succinic acid fermentation broth, $Mg^{2+}$ salt | Methanol | 5 | 210 | 400 | 49.2 | Temperature Variation |
| 3 | Succinic acid fermentation broth, $Mg^{2+}$ salt | Methanol | 5 | 230 | 400 | 72.4 | |
| B | | | | | | | |
| 1 | Succinic acid fermentation broth, $Mg^{2+}$ salt | Methanol | 5 | 180 | 400 | 13.9 | |

TABLE 4-continued

Variations in Reaction Conditions

| Example | Substrate | Alcohol | Reaction Time (h) | Temperature (° C.) | Initial CO$_2$ pressure (psi) | % Conversion to Diester | |
|---|---|---|---|---|---|---|---|
| 2 | Succinic acid fermentation broth, Mg$^{2+}$ salt | Methanol | 5 | 180 | 500 | 11.4 | Pressure Variation |
| 3 | Succinic acid fermentation broth, Mg$^{2+}$ salt | Methanol | 5 | 180 | 600 | 9.6 | |
| C | | | | | | | |
| 1 | Succinic acid fermentation broth, Mg$^{2+}$ salt | Methanol | 5 | 180 | 400 | 13.9 | |
| 2 | Succinic acid fermentation broth, Mg$^{2+}$ salt | Methanol | 2 | 180 | 400 | 5.4 | Reaction Time Variation |
| 3 | Succinic acid fermentation broth, Mg$^{2+}$ salt | Methanol | 0.5 | 180 | 400 | ND | |

TABLE 5

| Example | Substrate | Alcohol | Reaction Time (h) | Temperature (° C.) | Initial CO$_2$ pressure (psi) | % Conversion to Diester | Note |
|---|---|---|---|---|---|---|---|
| 1 | Succinic acid, Mg$^{2+}$ salt | Methanol | 5 | 210 | 400 | 33.4 | Control |
| 2 | Succinic acid, Mg$^{2+}$ salt | Ethanol | 5 | 180 | 400 | 1.0 | Limited solubility |
| 3 | Succinic acid, Co$^{2+}$ salt | Methanol | 5 | 180 | 400 | 1.3 | Limited solubility |
| 4 | Succinic acid | Methanol | 5 | 150 | 400 | 37.0 | |
| 5 | Succinic acid | Methanol | 5 | 180 | 400 | 81.2 | |
| 6 | Succinic acid | Ethanol | 5 | 180 | 400 | 60.8 | |
| 7 | Succinic acid | 1-Butanol | 5 | 180 | 400 | 52.2 | |
| 8 | Citric acid | Methanol | 5 | 180 | 400 | 20.1 | |
| 9 | Malic acid | Methanol | 5 | 180 | 400 | 86.3 | |

Table 5 lists results from other examples of esterification reactions according to the present method. Examples 1, 2 and 3 demonstrate the importance of substrate solubility of succinic acid as compared to the salts of succinate. Examples 4-7 is a second set of reactions in which free succinic acid was reacted in methanol, ethanol, and 1-butanol in similar fashion. Examples 8 and 9 show that reactions with other carboxylic acids, such as citric acid and malic acid can achieve relatively good yields of about 20% and 86%, respectively.

Free succinic acid reacts readily with the alcohols, since it is completely soluble in methanol, ethanol, butanol, and other alcohols up to and including octanol (C$_3$ alcohol). In Examples 6 and 7, succinic acid reacted in ethanol and 1-butanol, yields 60.8% and 52.2% conversion, respectively.

The solubility of carboxylic salts in a particular solvent can have an influence on the esterification process. The greater solubility of tree-acid permits a greater reactivity than the carboxylate salt, which lacks an acid functionality. Accordingly, the yields of the corresponding esters tend to be significantly greater than the control samples when comparing the two sets of reactions. The reactions of Examples 4-7 yielded significantly greater amounts of corresponding diesters than that of Examples 1-3. The carboxylic acid itself may be sufficient to catalyze the esterification reaction under the present operational temperature and pressure conditions. One can adjust the substrate solubility tor successful esterification according to the present method.

The present invention has been described in general and in detail by way of examples. Persons of skill in the art understand that the invention is not limited necessarily to the embodiments specifically disclosed, but that modifications and variations may be made without departing from the scope of the invention as defined by the following claims or their equivalents, including other equivalent components presently known, or to be developed, which may be used within the scope of the present invention. Therefore, unless changes otherwise depart from the scope of the invention, the changes should be construed as being included herein.

We claim:

1. A process for recovering and using carboxylic acids from a fermentation broth, the process comprises: a) obtaining a fermentation broth having an adjusted pH of less than 5, containing at least one free carboxylic acid or a mixture of carboxylic acids, or at least one free carboxylic acid and an associated alkali or alkaline earth metal salts thereof; b) drying said fermentation broth containing free carboxylic acid into a powder; and c) synthesizing an ester by reacting said carboxylic acid in said powder with an alcohol solvent under a CO$_2$ atmosphere in substantial absence of any other acid catalyst at either a reaction temperature or pressure or both which corresponds to supercritical, critical, or near critical conditions for at least one of said alcohol or CO$_2$.

2. The process according to claim 1, further comprising converting said ester back to a free carboxylic acid.

3. The process according to claim 1, wherein said fermentation broth contains cell mass and insoluble compounds and further comprises filtering said fermentation broth to remove said cell mass and insoluble compounds either before drying or after ester synthesis.

4. The process according to claim 1, further comprising concentrating said ester.

5. The process according to claim 3, wherein said fermentation broth is either (a) part of a continuous fermentation process, and further comprising recycling said insoluble compounds back into said fermentation broth; or (b) part of a batch fermentation process, and further comprising recycling said insoluble compounds into a second fermentation reactor.

6. The process according to claim 1, wherein said alcohol has an R-group of $C_1$-$C_{20}$ that is at least a saturated, unsaturated, cyclic, or aromatic species.

7. The process according to claim 1, wherein said carboxylic acid is selected from: formic acid, acetic acid, propionic acid, lactic acid, butyric acid, isobutyric acid, valeric acid, hexanoic acid, heptanoic acid, decanoic acid, lauric acid, myristic acid, and $C_{15}$-$C_{18}$ fatty acids, fumaric acid, itaconic acid, malic acid, succinic acid, maleic acid, malonic acid, glutaric acid, glucaric acid, oxalic acid, adipic acid, pimelic acid, suberic acid, azelaic acid, sebacic acid, dodecanedioic acid, glutaconic acid, ortho-phthalic acid, isophthalic acid, terephthalic acid, citric acid, isocitric acid, aconitic acid, tricarballylic acid, and trimesic acid.

8. The process according to claim 1, wherein said carboxylic acid is a polycarboxylic acid.

9. The process according to claim 1, wherein said reaction temperature is between about 150° C. and about 250° C., and said pressure is between about 400 psi and 3,000 psi (2758 KPa and 20684 KPa).

10. The process according to claim 1, wherein said free carboxylic acids are not subject to activation with a halide to form an acyl halide.

11. The process according to claim 1, wherein said fermentation broth is at a pH in a range between about 1.5 and about 4.5.

12. The process according to claim 1, wherein said mixture of free carboxylic acid contains at least a diacid, triacid, or polyacid, and said reaction with alcohol yields a minimum of 50% conversion of said diacid, triacid, or polyacid to a corresponding ester of the free carboxylic acid.

13. The process according to claim 1, wherein said process further comprising purifying said ester to at least about 90% purity.

14. The process according to claim 1, further comprises subjecting said ester to hydrogenation to produce a compound selected from one of the following: 1,4-butane-diol (BDO), tetrahydrofuran (THF), γ-butyrolactone (GBL), or N-Methyl-2-pyrrolidone (NMP).

15. The process according to claim 1, further comprises subjecting said ester to hydrogenation or hydrogenolysis to produce a biofuel compound.

16. The process according to claim 1, wherein the ester is further converted into pharmaceutical, cosmetic, food or feed ingredient, or polymer materials.

17. The process according to claim 1, wherein said dried fermentation broth powder is shipped to a location different from where said fermentation broth is sourced; or said reaction for ester synthesis is performed at a remote location different from where said fermentation broth is sourced.

18. An esterification method for a polycarboxylic acid comprising: providing a solution of at least one free carboxylic acid from a fermentation broth having an adjusted pH of less than 5; reacting said solution of free carboxylic acids with an alcohol in $CO_2$ atmosphere without any other acid catalyst; and selecting an operational reaction temperature or a reaction pressure corresponding to supercritical, critical or near critical conditions for at least one of said alcohol or $CO_2$ to yield an ester corresponding to said free carboxylic acid.

19. The esterification method according to claim 18, wherein said reaction temperature and pressure conditions drive said reaction towards formation of diester molecules over monoester molecules when the carboxylic acid is a polyacid.

20. The esterification method according to claim 18, wherein said reaction temperature is between about 150° C. and about 250° C., and said reaction pressure is between 400 psi and about 3,000 psi (2758 KPa and 20684 KPa), and said reaction is run for up to about 12 hours.

21. The esterification method according to claim 18, wherein said polycarboxylic acid is selected from: fumaric acid, itaconic acid, malic acid, succinic acid, maleic acid, malonic acid, glutaric acid, glucaric acid, oxalic acid, adipic acid, pimelic acid, suberic acid, and azelaic acid, sebacic acid, dodecanedioic acid, glutaconic acid, ortho-phthalic acid, isophthalic acid, terephthalic acid, citric acid, isocitric acid, aconitic acid, tricarballylic acid, and trimesic acid.

22. The esterification method according to claim 18, wherein said solution of free carboxylic acids further includes alkali or alkaline earth metal salts of said carboxylic acids.

23. A method of processing an agricultural product or biomass, comprising: obtaining carbohydrates from said agricultural product or biomass; fermenting said carbohydrates to produce a fermentation broth, said fermentation broth having an adjusted pH of less than 5; drying said fermentation broth to produce a fermentation broth powder; transporting said fermentation broth powder to a second processing site; and reacting at least a free carboxylic acid or a mixture of free carboxylic acids and associated salts thereof in said dried fermentation broth at said second processing site with an alcohol solvent under a $CO_2$ atmosphere in substantial absence of any other extrinsic catalyst at a reaction temperature and pressure that corresponds to supercritical, critical or near critical conditions for at least the alcohol or $CO_2$ to synthesize an ester.

24. The method according to claim 23, wherein said second processing site is located nearer to a source of demand for a product derivable from said fermentation broth powder.

25. The method according to claim 23, further comprising transforming said synthesized ester to produce a product therefrom.

26. The process according to claim 6, wherein said alcohol is a $C_2$-$C_6$-diol.

27. The process according to claim 8, wherein said polycarboxylic acid is a dicarboxylic or a tricarboxylic acid.

28. The esterification method according to claim 20, wherein said reaction temperature is in a range between about 180° C. and about 245° C., and said reaction pressure is between about 950 psi and about 2,400 psi (6550 KPa and 16547 KPa).

* * * * *